(12) United States Patent
Ferro et al.

(10) Patent No.: US 12,279,797 B2
(45) Date of Patent: Apr. 22, 2025

(54) U-BLOQ CHEST WALL SYSTEM

(71) Applicant: PAMPAMED SRL, Buenos Aires (AR)

(72) Inventors: Marcelo Hernan Martinez Ferro, Buenos Aires (AR); Gaston Bellia-Munzon, Buenos Aires (AR)

(73) Assignee: PAMPAMED SRL, Buenos Aires (AR)

( * ) Notice: Subject to any disclaimer, the term of this patent is extended or adjusted under 35 U.S.C. 154(b) by 1119 days.

(21) Appl. No.: 17/045,681

(22) PCT Filed: Apr. 9, 2019

(86) PCT No.: PCT/EP2019/058924
§ 371 (c)(1),
(2) Date: Oct. 6, 2020

(87) PCT Pub. No.: WO2019/197391
PCT Pub. Date: Oct. 17, 2019

(65) Prior Publication Data
US 2021/0022782 A1 Jan. 28, 2021

Related U.S. Application Data

(60) Provisional application No. 62/655,532, filed on Apr. 10, 2018, provisional application No. 62/699,486, filed on Jul. 17, 2018.

(51) Int. Cl.
*A61B 17/80* (2006.01)
(52) U.S. Cl.
CPC ........ *A61B 17/8076* (2013.01); *A61B 17/808* (2013.01)

(58) Field of Classification Search
CPC .............. A61B 17/7086; A61B 17/823; A61B 17/7049; A61B 17/705
See application file for complete search history.

(56) References Cited

U.S. PATENT DOCUMENTS

| 6,669,697 | B1 * | 12/2003 | Pisharodi | ............. | A61B 17/701 606/264 |
| 9,833,269 | B2 * | 12/2017 | Park | .................. | A61B 17/8076 |
| 9,872,708 | B2 * | 1/2018 | Park | .................. | A61B 17/8869 |
| 10,531,901 | B2 * | 1/2020 | Su | ...................... | A61B 17/8023 |

(Continued)

FOREIGN PATENT DOCUMENTS

| CN | 106691565 A | * | 5/2017 |
| KR | 101037957 | | 5/2011 |

(Continued)

OTHER PUBLICATIONS

Translation of CN106691565.*
Translation WO2017023147 A1.*

*Primary Examiner* — Lynnsy M Summitt
(74) *Attorney, Agent, or Firm* — LUMEN PATENT FIRM

(57) ABSTRACT

A flail chest stabilization device is provided that includes a pair of lateral bridges, a pair of main stabilization bars, a screw and slider-element connector assembly, and a slider introducer tool, where the slider introducer tool positions the slider-element, where the main stabilization bars are connected by the screw and slider connector assembly to the lateral bridges, where the stabilization bars are in a parallel configuration or crossed configuration.

11 Claims, 18 Drawing Sheets

(56) References Cited

U.S. PATENT DOCUMENTS

| | | | | |
|---|---|---|---|---|
| 10,835,293 B2 * | 11/2020 | Pisharodi | ............ | A61B 17/7043 |
| 2004/0117016 A1 * | 6/2004 | Abramson | ......... | A61B 17/8076 |
| | | | | 606/71 |
| 2011/0251540 A1 * | 10/2011 | Notrica | .............. | A61B 17/8076 |
| | | | | 602/19 |
| 2017/0156759 A1 | 6/2017 | Park | | |
| 2018/0310973 A1 * | 11/2018 | Son | .................... | A61B 17/8076 |
| 2019/0314072 A1 * | 10/2019 | Uemura | ............. | A61B 17/8076 |

FOREIGN PATENT DOCUMENTS

| | | | | |
|---|---|---|---|---|
| KR | 1018524440000 | | 4/2018 | |
| WO | WO-2017023147 A1 * | 2/2017 | ............. | A61B 17/56 |

* cited by examiner

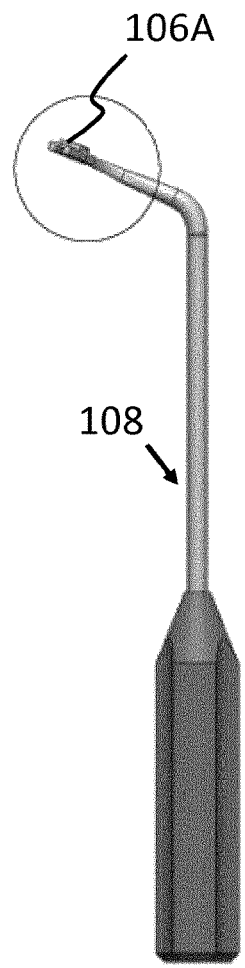
FIG. 2A
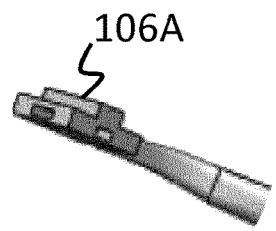
FIG. 2B
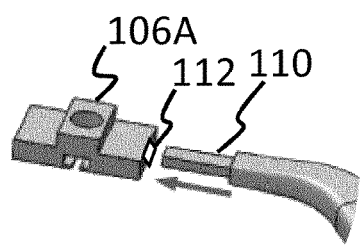
FIG. 2C
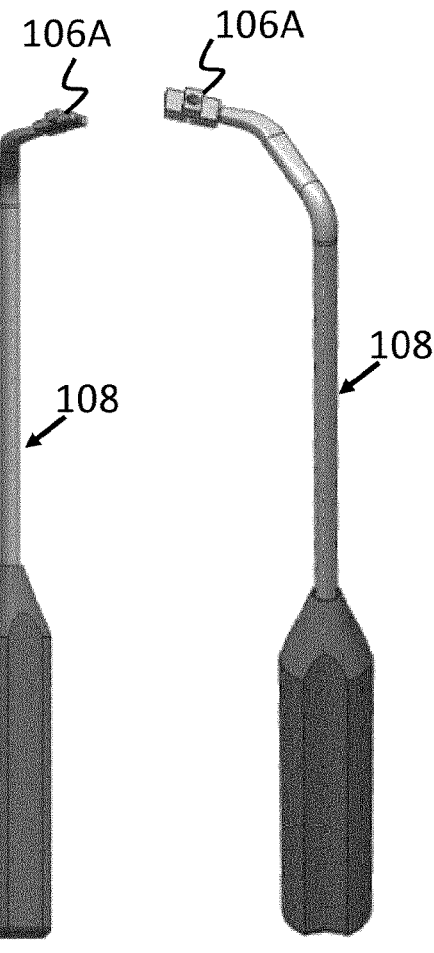
FIG. 2D   FIG. 2E
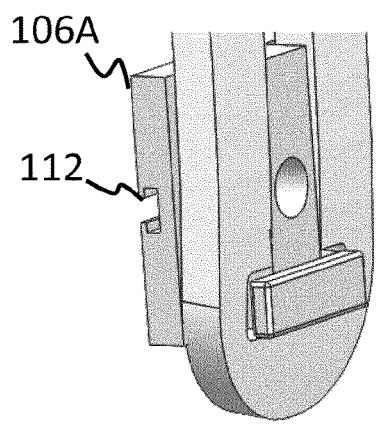
FIG. 2F

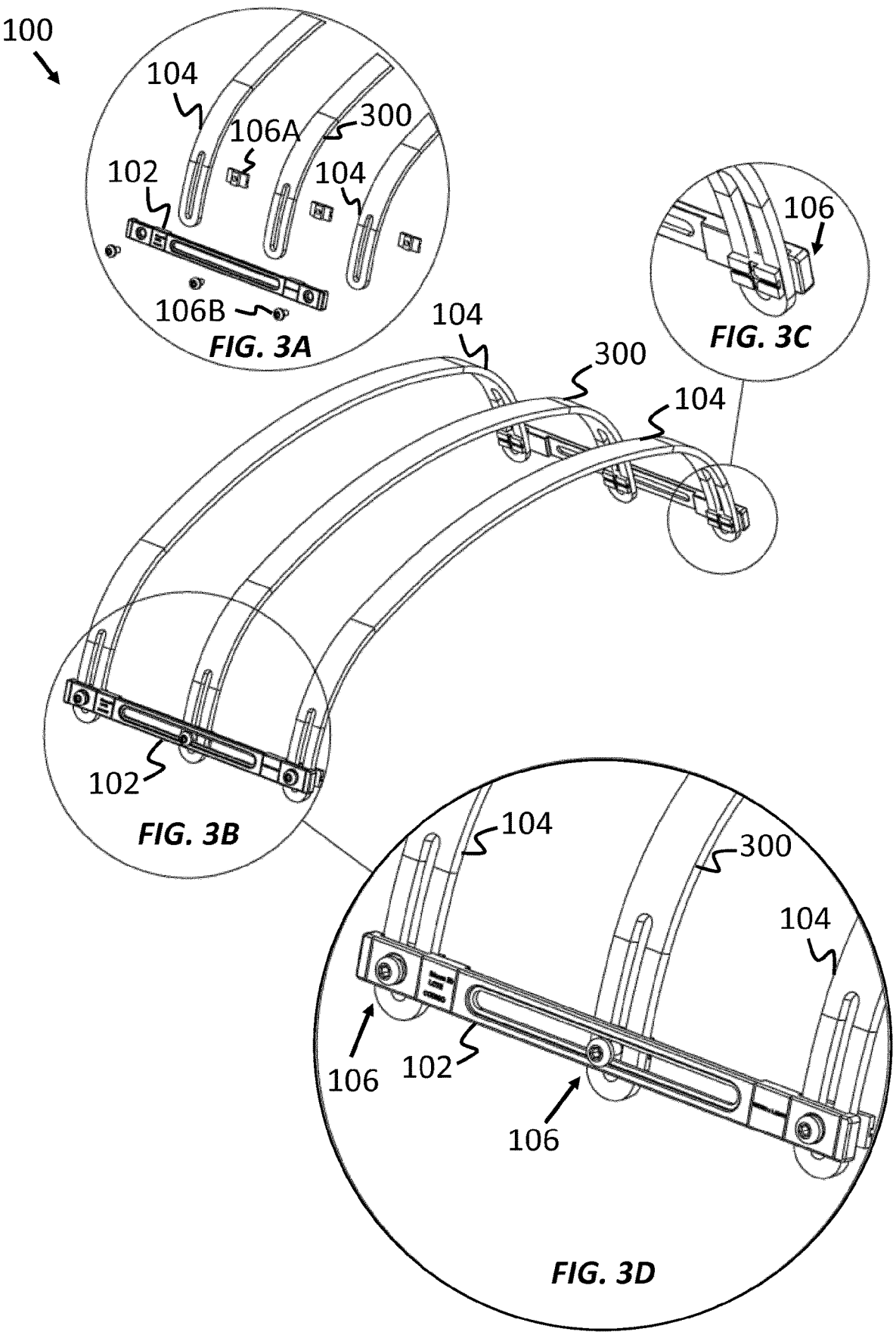

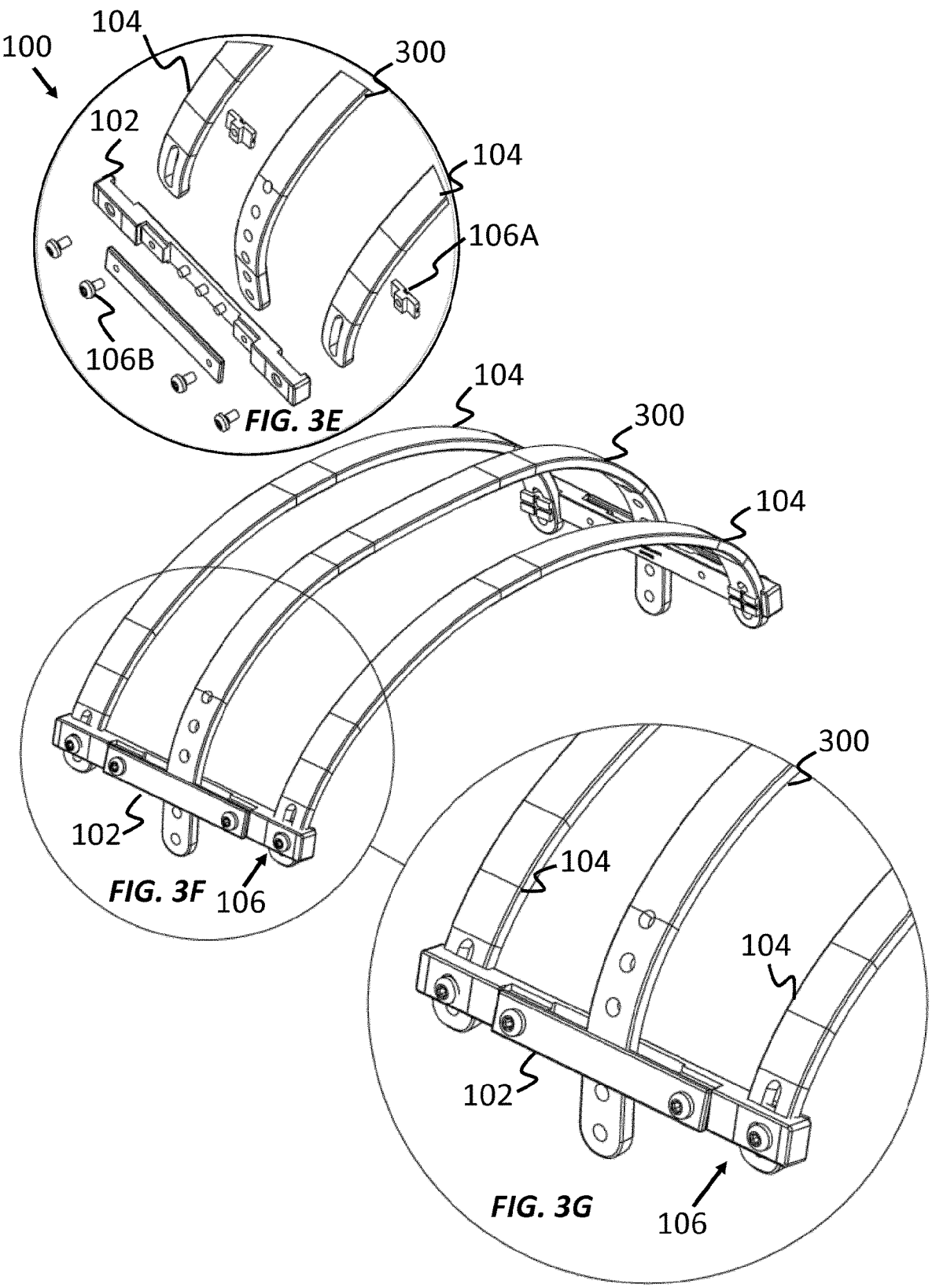

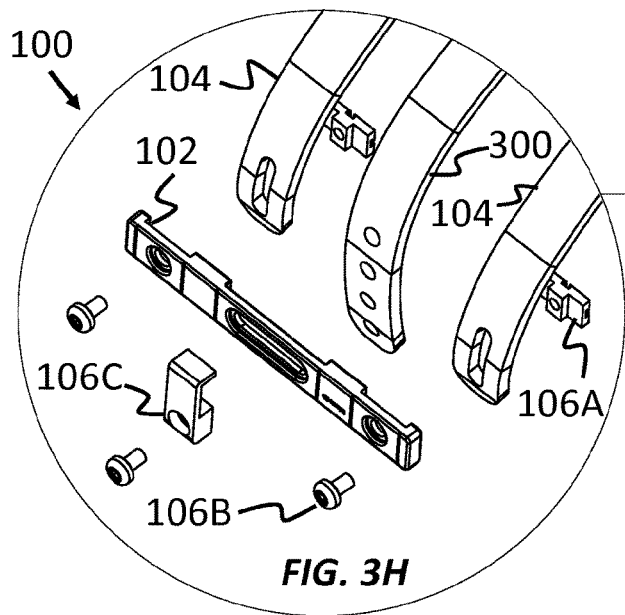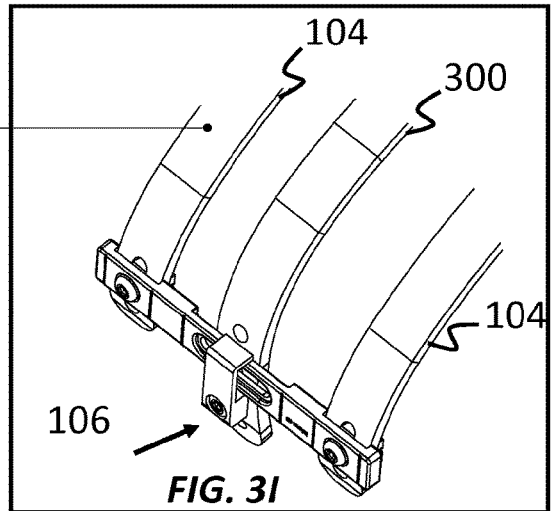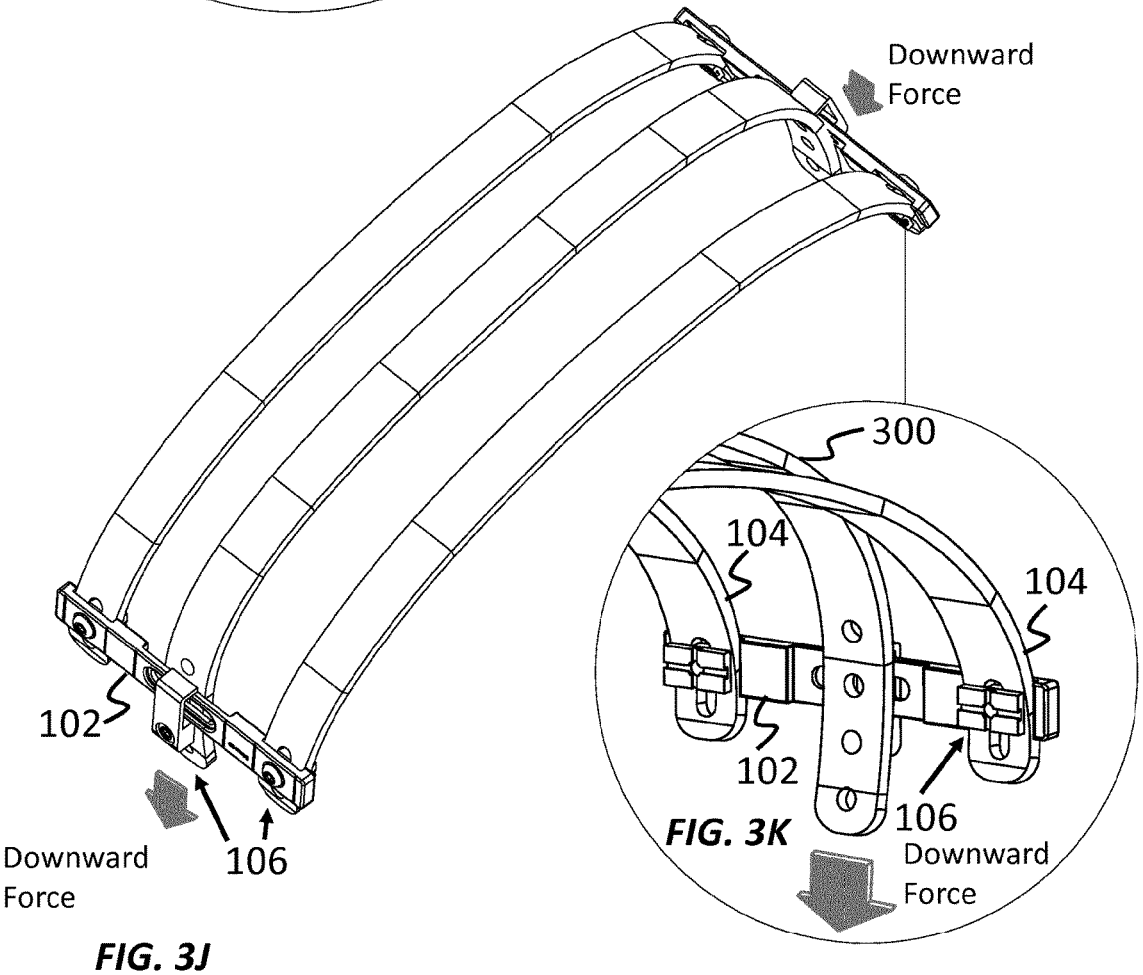
*FIG. 3H*
*FIG. 3I*
*FIG. 3J*
*FIG. 3K*

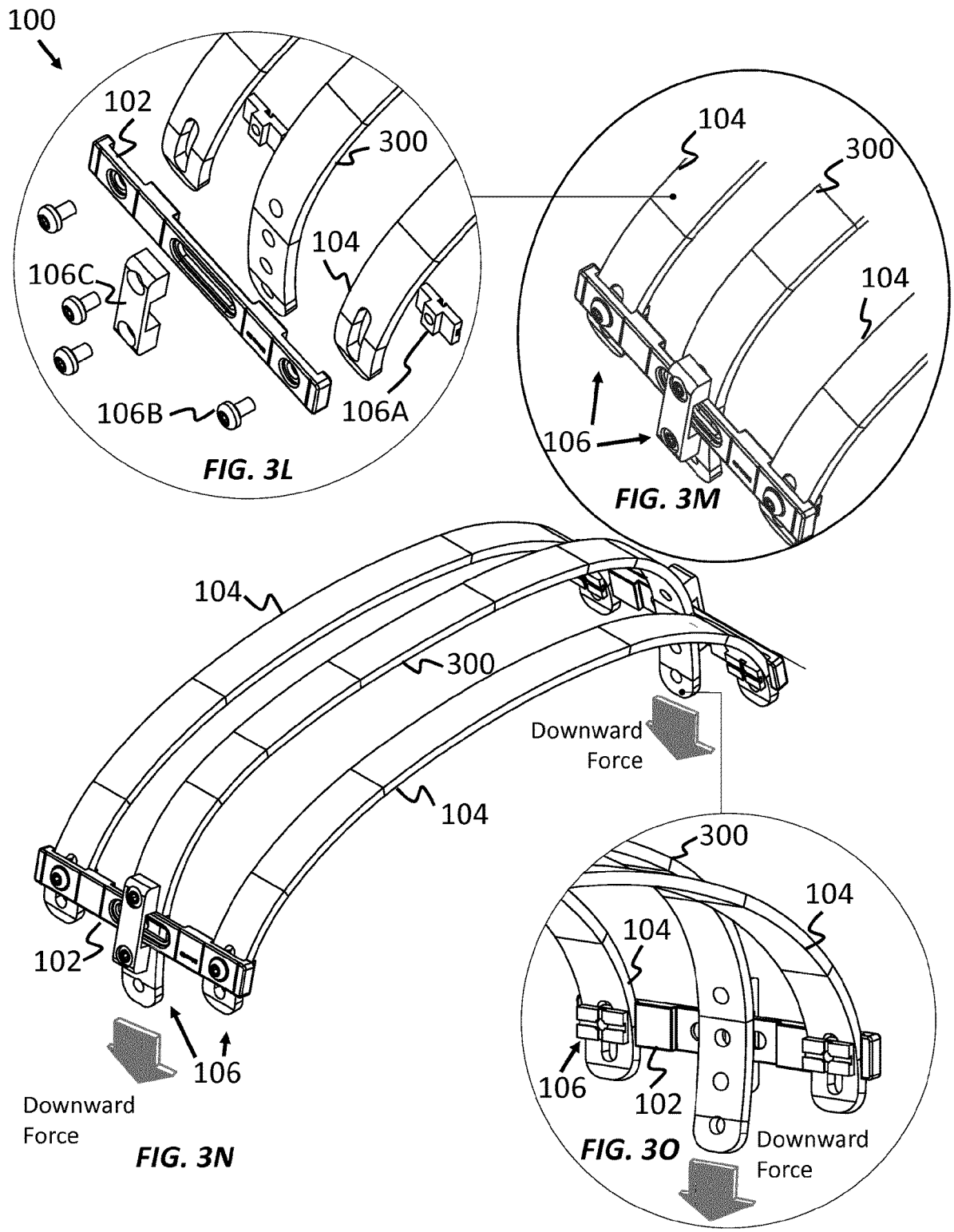

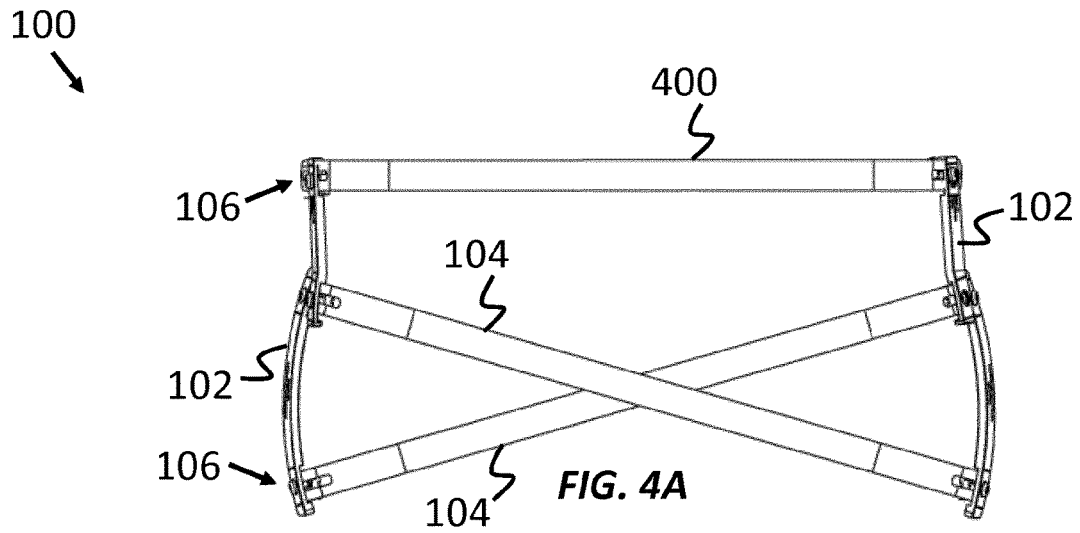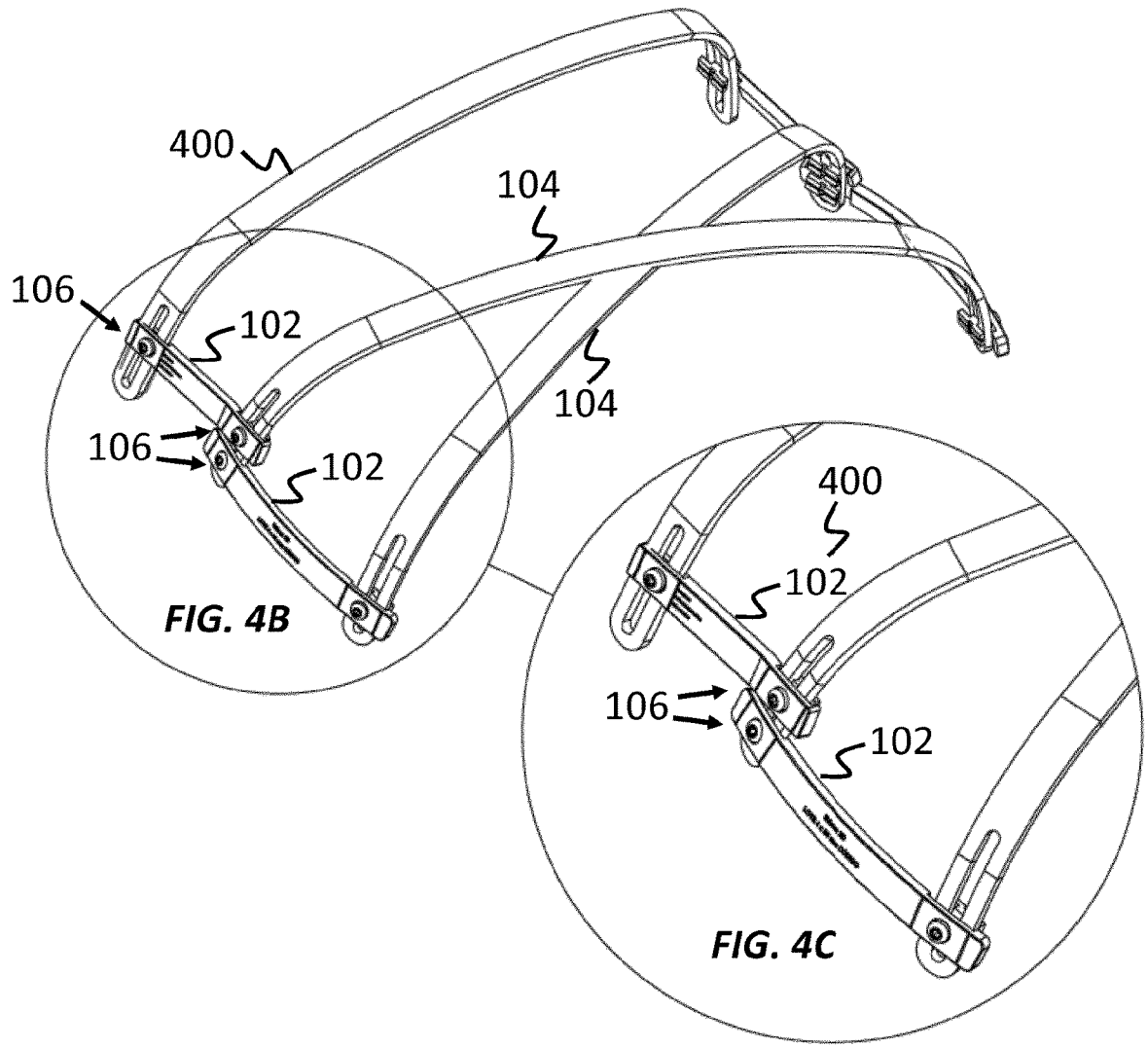

100

U-BLOQ CHEST WALL SYSTEM

FIELD OF THE INVENTION

The present invention relates generally to surgical stabilization of flail chest, chest wall bone fractures after trauma and/or the correction of chest wall deformities. More particularly, the invention relates to severe chest wall trauma and complex deformities of the anterior chest wall that need to be stabilized and/or corrected surgically by means of chest wall remodeling and surgical stabilization.

BACKGROUND OF THE INVENTION

Flail chest is a life-threatening medical condition that occurs when a segment of the rib cage breaks due to trauma and becomes detached from the rest of the chest wall.

What is needed is a flail chest stabilization device that implants to a patient's body without connecting to a muscle, a rib or any surrounding tissue.

SUMMARY OF THE INVENTION

To address the needs in the art, a flail chest stabilization device is provided that includes a pair of lateral bridges, a pair of main stabilization bars, a screw and slider-element connector assembly, and a slider introducer tool, where the slider introducer tool positions the slider-element, where the main stabilization bars are connected by the screw and slider connector assembly to the lateral bridges, where the stabilization bars are in a parallel configuration or crossed configuration.

According to one aspect of the invention, the main stabilization bar is thicker in a center region relative to each end region, where the thicker center region imparts a central stabilization force that is greater than an end stabilization force.

In another aspect of the invention, the main stabilization bar includes a T-shape slot or a linear shape slot at each end. In one aspect, the slider-element further includes a spoiler block configured to limit a range of travel for the slider-element within the stabilization bar T-shape slot, where the screw and slider element assembly are moveably engaged with the T-shape slot or the linear shape slot.

In a further aspect, the invention includes a middle stabilization bar connected to the lateral bridges, where the middle stabilization bar is configured to provide antero-posterior stabilization. In one aspect, the middle stabilization bar includes a single thickness from end to end, where the middle stabilization bar has a plurality multiple threaded holes, or slots on each the end. In a further aspect, the middle stabilization bar is configured to impart a force that goes from front to back of a rib cage, where the imparted force flattens asymmetric deformities or stabilizes fractured bones. In another aspect, the middle bar is connected to the lateral bridges by lateral secondary mini-bridges, where the lateral secondary mini-bridges are connected to the lateral bridges by the screw and slider-element connector assembly, where the middle stabilization bar is connected to the secondary mini-bridge by a threaded screw.

In yet another aspect of the invention, the flail chest stabilization device implants to a patient's body without connecting to a muscle, a rib or any surrounding tissue.

According to one aspect of the invention, the lateral bridges include a flat or curved profile. In one aspect, the invention further includes a superior parallel stabilization bar, where the main stabilization bars are connected to the curved lateral in the crossed configuration, where the superior parallel stabilizer bar is connected to the flat lateral bridges, where the flat lateral bridges are further connected to the main stabilization bars.

According to another aspect of the invention, the slider introducer tool is positioned under the main stabilization bar during a surgical procedure.

BRIEF DESCRIPTION OF THE DRAWINGS

FIGS. 2A-2F show how the slider introducer tool engages the slider-element by inserting an introducer tip into a slider-element port, according to one embodiment of the invention.

FIGS. 4A-4C show a superior parallel stabilization bar are connected to the curved lateral bridges in the crossed configuration, according to the current invention.

DETAILED DESCRIPTION

The current invention is a device for the stabilization of flail chest, including multiple chest wall bone fractures and/or the correction of deformities of the anterior chest wall.

The system according to the current invention is different because it avoids fixation of the implants to the patient's body parts (muscles, ribs and surrounding tissues) as the system fixates by its own. The fixation method is original (sliders, bridges and screws). Also the possibility of crossed main stabilization bars with original curved bridges are innovative. The crossed stabilization bars can be combined to a superior parallel stabilization bars, thus the fixation system requires a combined curved-straight bridges.

This is a system comprised of main stabilization bars that can be parallel or crossed and are fixed laterally by bridges.

The main stabilization bar is thicker in the center where mayor forces are required and thinner in both ends where less stabilization forces are required.

There are two models of main stabilization bars, with (T shape slot) or without horizontal slot depending on the model of slider to be used.

The main lateral bridges are fixed by means of sliders and screws. There are two model of sliders, with and without spoiler. The slider with spoiler is intended to be used with the main stabilization bar that has T shaped slots.

In certain complex thoracic deformities or extremely severe chest trauma with sternal fractures that need mixed stabilization forces (anterior and posterior forces) a novel three bars system in which the middle bar and the lateral bridges provide combined antero-posterior stabilization has been designed.

In this specific variant, the middle bar has the same thickness from end to end and has a fixation method comprised of multiple threaded holes on each end. This middle bar is used to apply a force that goes from front to back in order to flatten asymmetric deformities or stabilize fractured bones such as the sternum. In order to fix this middle bar, two lateral secondary mini-bridges are fixed to the middle bar by means of one or two screws. Screws are placed into the threaded holes located at the end of the middle bar. The main bridges are used as an anchor for the middle bar fixation by means of the secondary mini-bridges.

Special original and innovative instrumentation has been designed for the delivery and placement of the sliders called "sliders introducers" that need to be placed under the main stabilization bar during the surgical procedure.

Figure 1A:
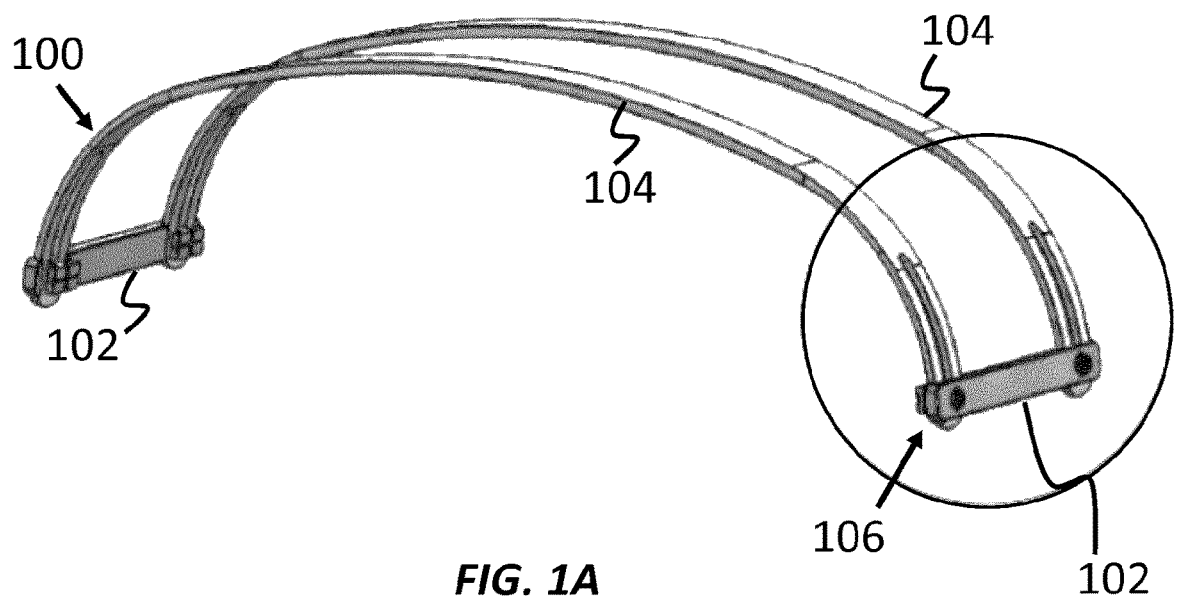
FIGS. 1A-1G show one embodiment of a flail chest stabilization device.
Figure 1B:
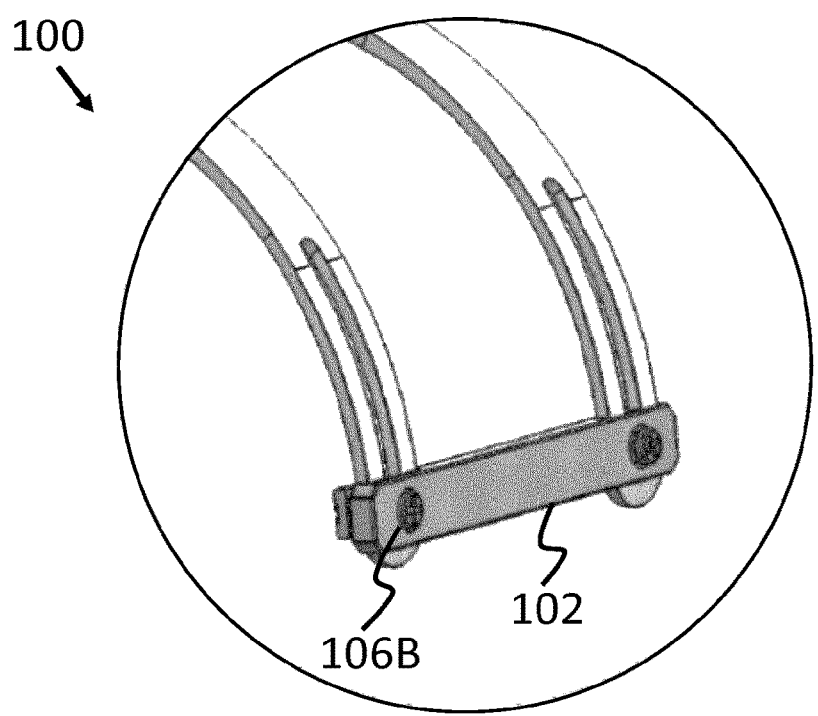
Figure 1C:
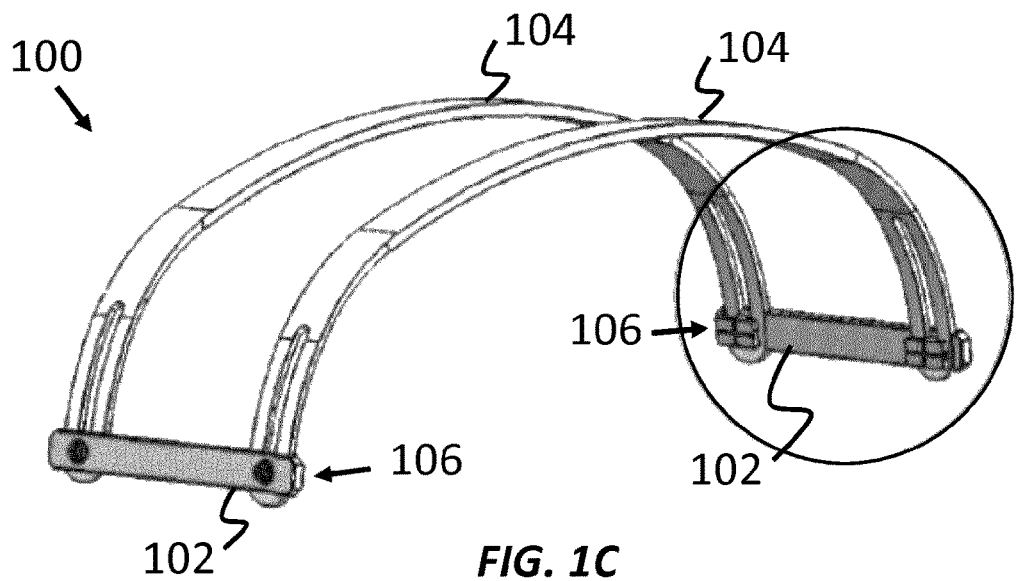
Figure 1D:
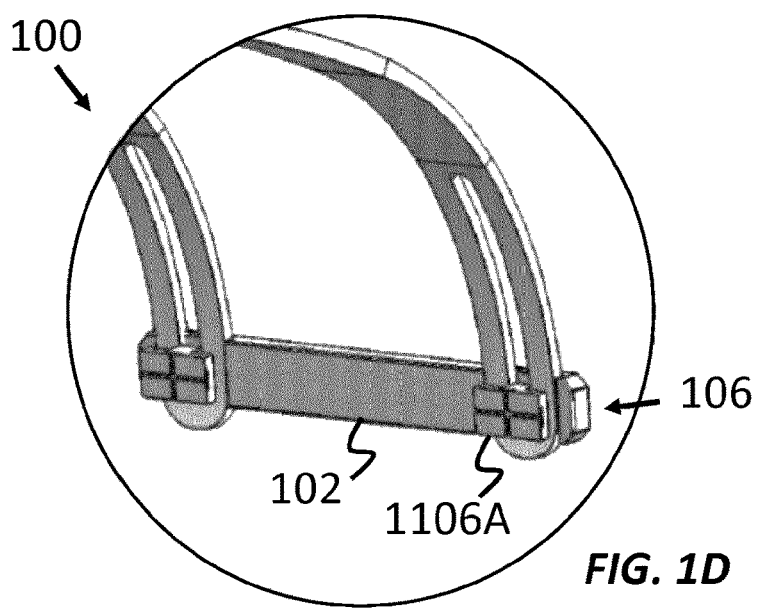
Figure 1E:
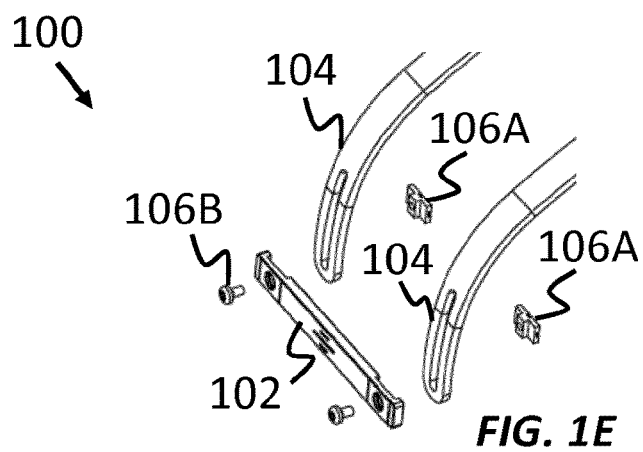
Figure 1F:
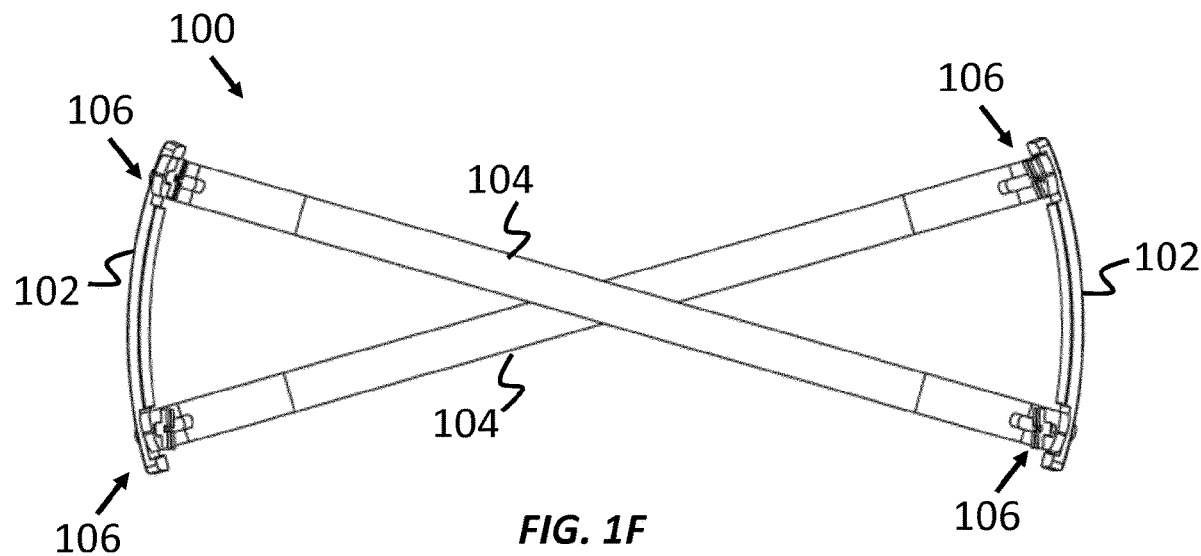

Turning now to the figures, one embodiment of a flail chest stabilization device 100 is provided in FIGS. 1A-1G, that includes a pair of lateral bridges 102, a pair of main stabilization bars 104, a screw and slider-element connector assembly 106, and a slider introducer tool 108, where the slider introducer tool 108 positions the slider-element 106A, where the main stabilization bars 102 are connected by the screw 106B and slider connector 106A assembly 106 to the lateral bridges 102, where the stabilization bars 104 are in a parallel configuration or crossed configuration (see FIG. 1F). As shown, lateral bridges 102 include a flat or curved profile.

Figure 1G:
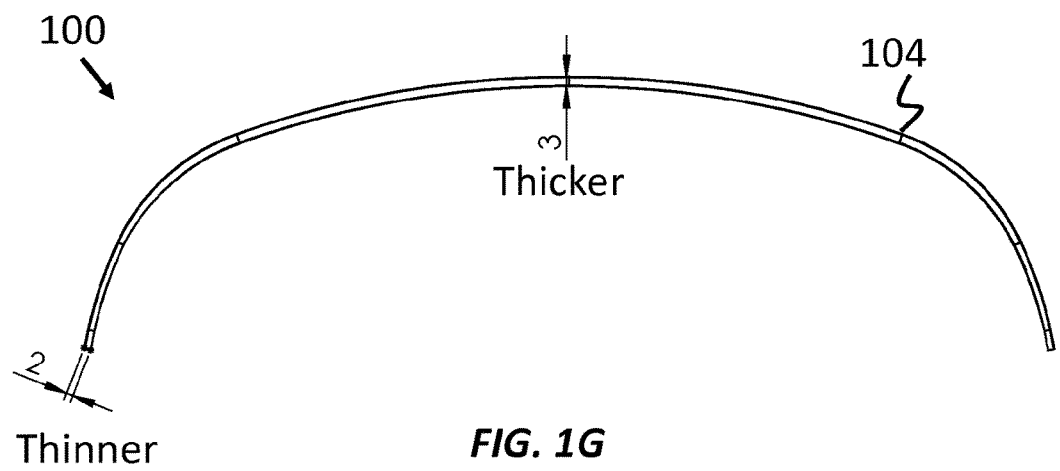

FIG. 1G shows the main stabilization bar 104 is thicker in a center region relative to each end region, where the thicker center region imparts a central stabilization force that is greater than an end stabilization force.

According to another aspect of the invention, the slider introducer tool 108 is positioned under the main stabilization bar 104 during a surgical procedure, where there are two different model of slider introducers, a left handed and a right handed. The slider introducer tool engages the slider-element 106A by inserting an introducer tip 110 into a slider-element port 112, as shown in FIGS. 2A-2E.

Figure 3P:
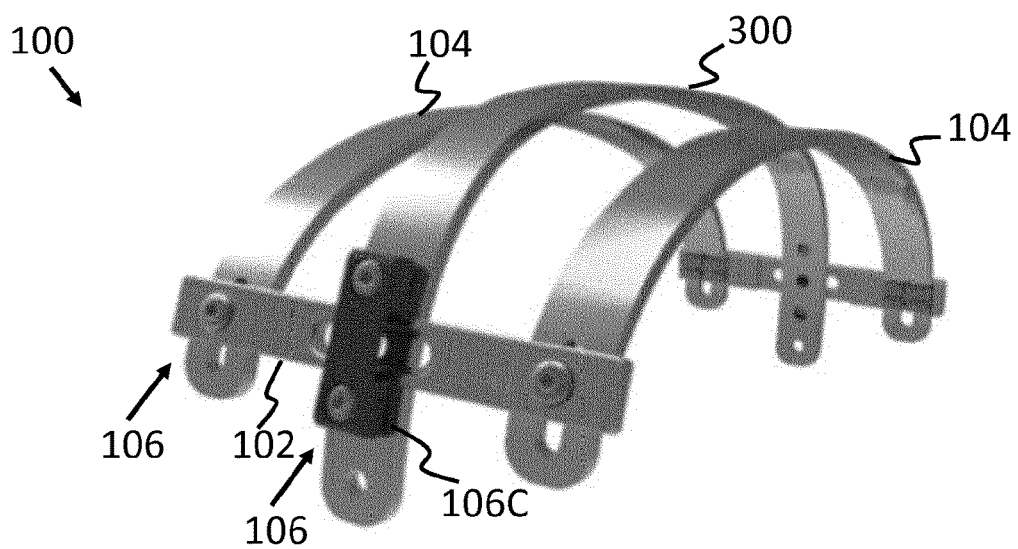
FIGS. 3A-3S show a middle stabilization bar connected to the lateral bridges, where the middle stabilization bar is configured to provide antero-posterior stabilization, where (3P-3S) show an assembled structure with a representative implementation, according to one embodiment of the invention.
Figure 3Q:
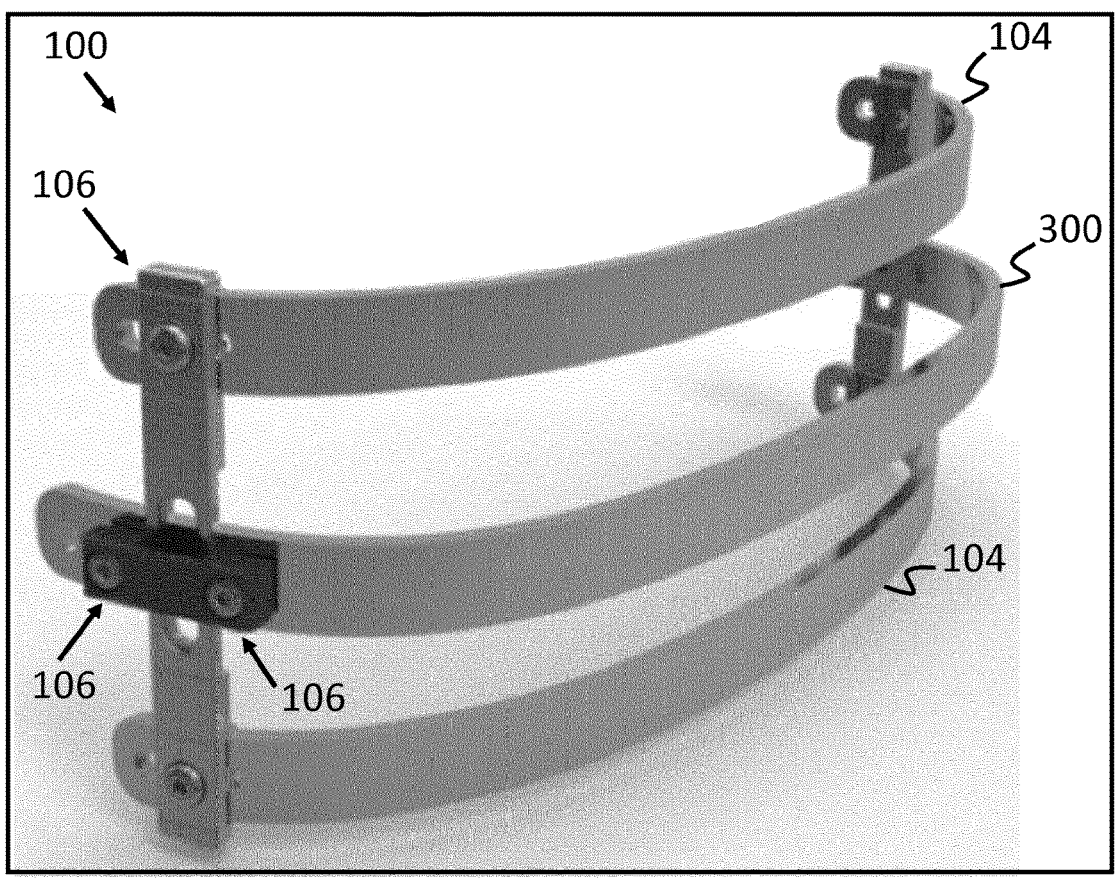
Figure 3R:
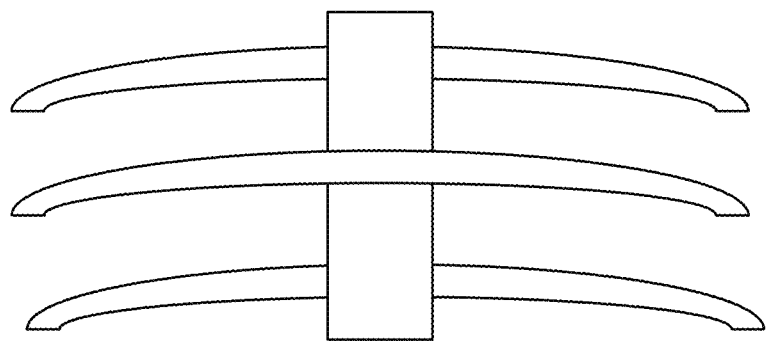
Figure 3S:
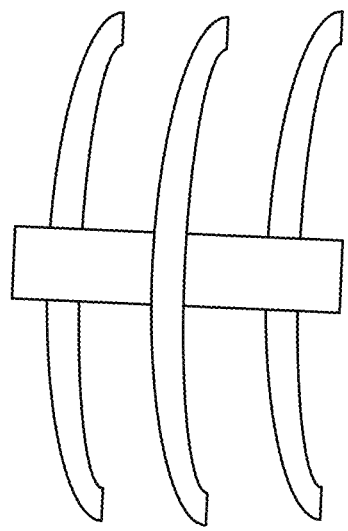

FIGS. 3A-3S show further embodiments, where the invention includes a middle stabilization bar 300 connected to the lateral bridges 102, where the middle stabilization bar 300 is configured to provide antero-posterior stabilization. In one aspect, the middle stabilization bar includes a single thickness from end to end, where the middle stabilization bar has a plurality multiple threaded holes, or slots on each end. In a further aspect, the middle stabilization bar is configured to impart a force that goes from front to back of a rib cage, where the imparted force flattens asymmetric deformities or stabilizes fractured bones. In another aspect, the middle bar is connected to the lateral bridges by lateral secondary mini-bridges 302, where the lateral secondary mini-bridges 302 are connected to the lateral bridges 102 by the screw and slider-element connector assembly 106, where the middle stabilization bar 300 is connected to the secondary mini-bridge 302 by a threaded screw. In the embodiments shown in FIGS. 3H-3S, the middle stabilization bar 300 is connected to the lateral bridges 102 using a bracket 106C, where the middle stabilization bar is disposed to exert a downward force on the chest, relative to the other main stabilization bars 104.

In a further embodiment, FIGS. 4A-4C show the invention further includes a superior parallel stabilization bar 400, where the main stabilization bars 103 are connected to the curved lateral bridges 102 in the crossed configuration, where the superior parallel stabilizer bar is connected to the flat lateral bridges 102, where the flat lateral bridges 102 are further connected to the main stabilization bars 104.

Figure 5A:
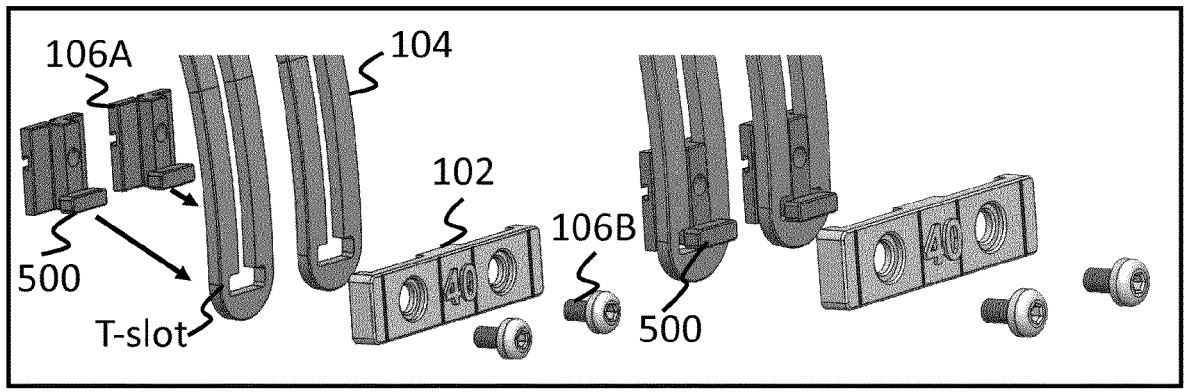
FIGS. 5A-5O show the main stabilization bar includes a T-shape slot with the slider-element further having a spoiler block configured to limit a range of travel for the slider-element within the stabilization bar T-shape slot, according to the current invention.
Figure 5B:
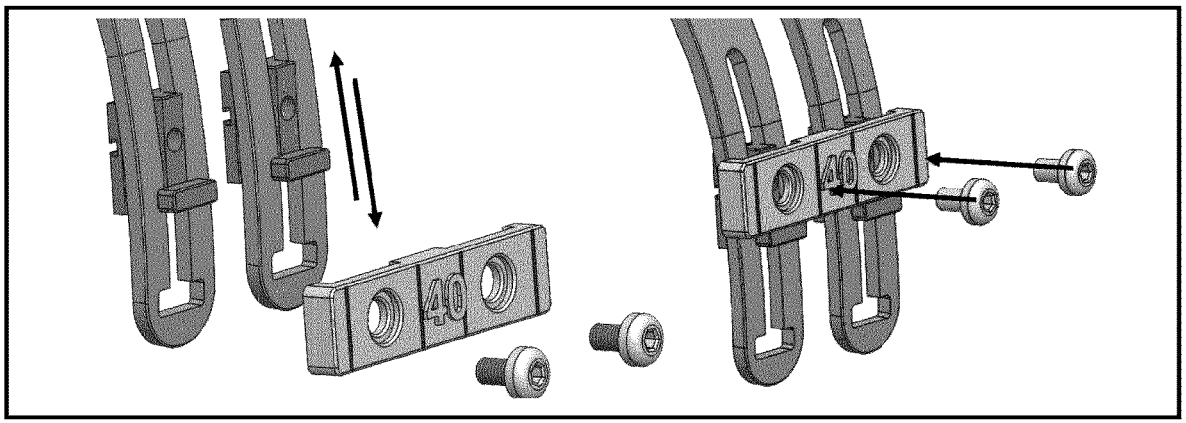
Figure 5C:
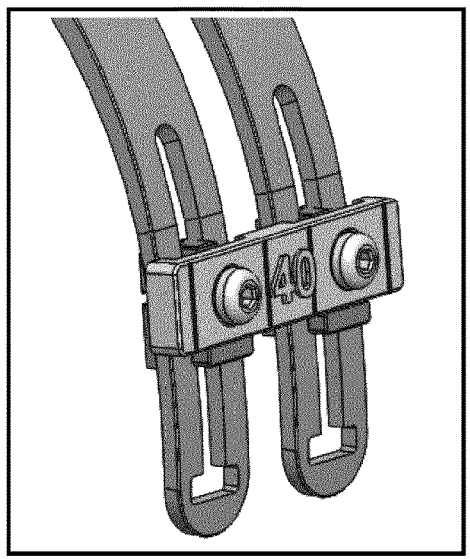
Figure 5D:
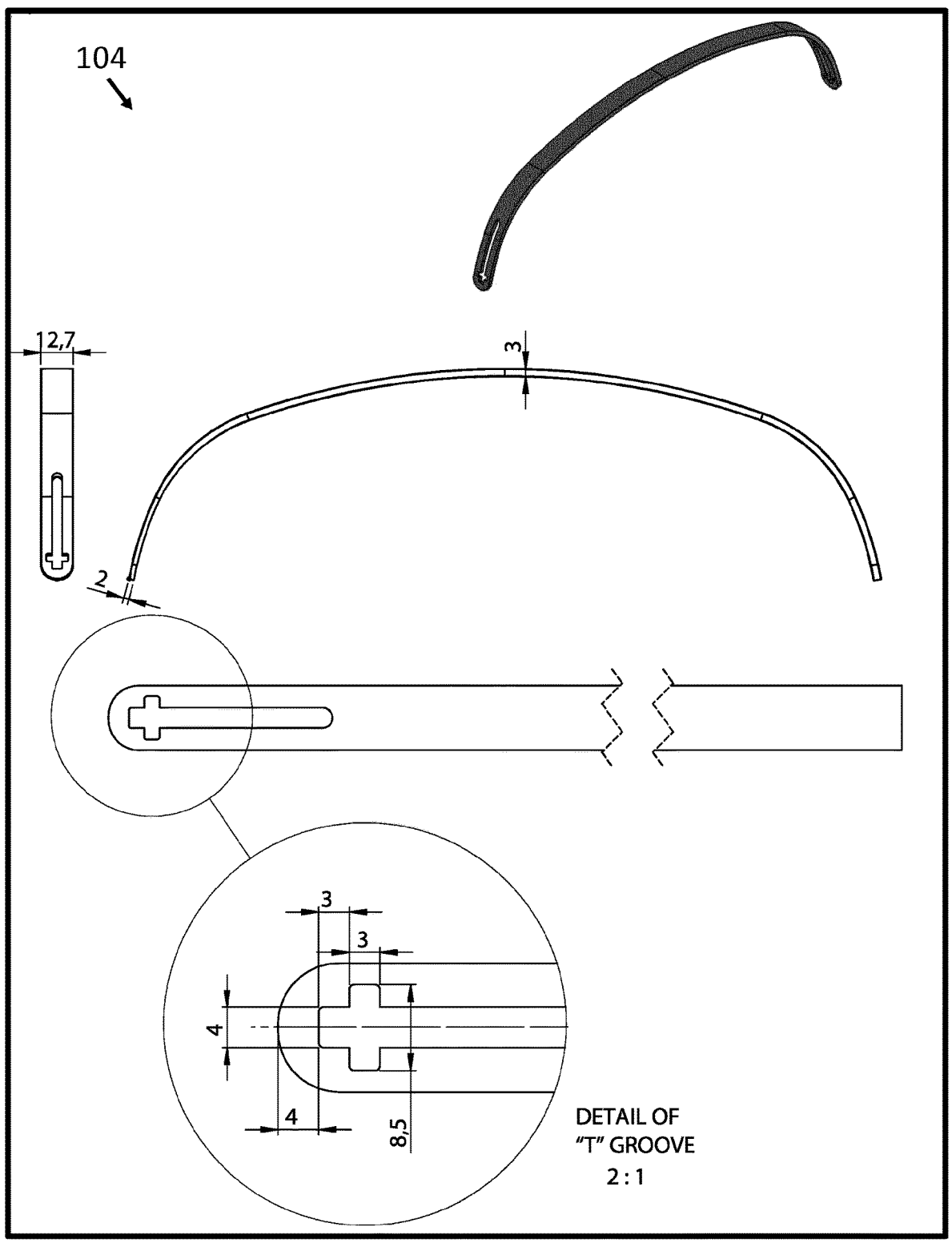
Figure 5E:
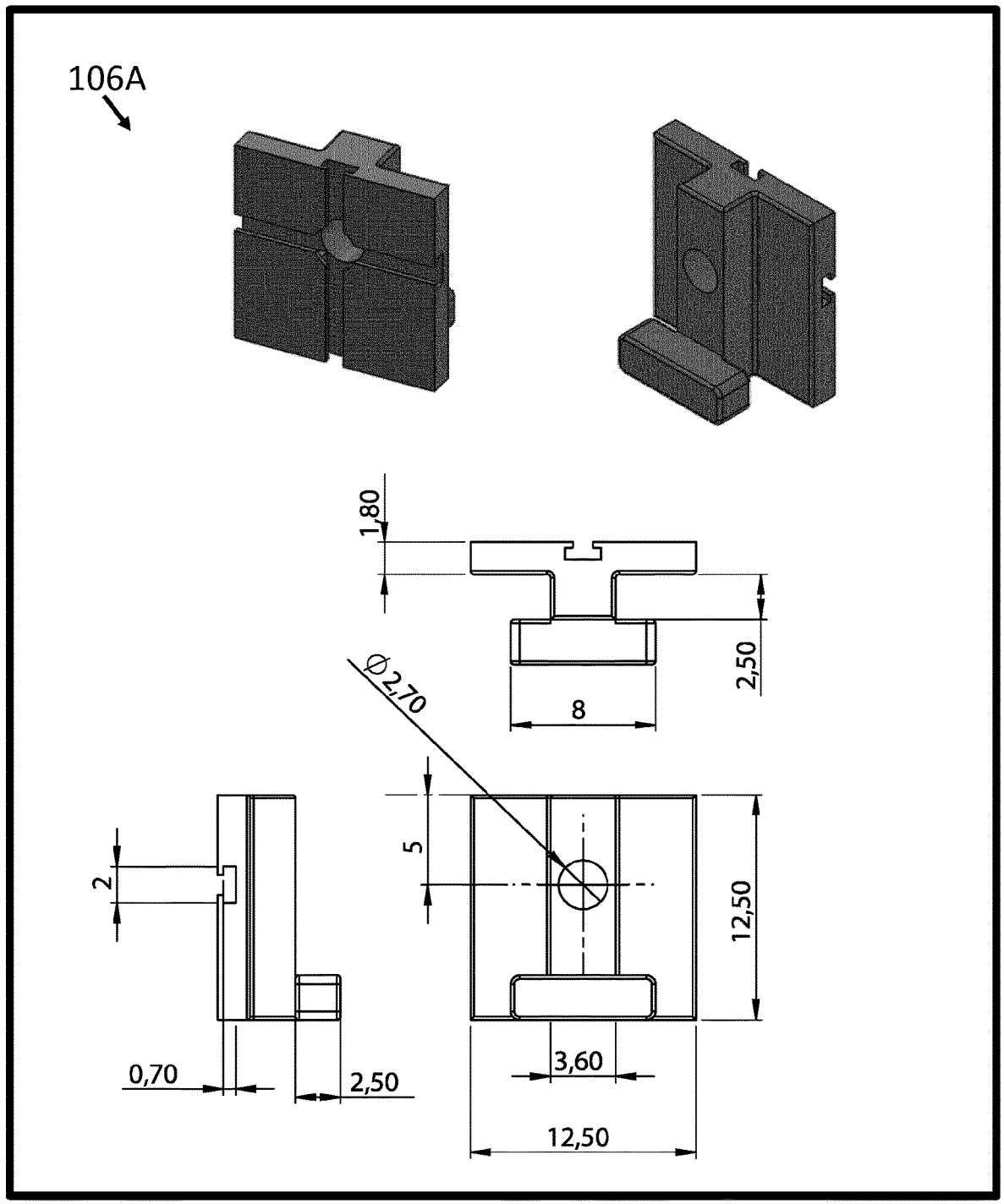
Figure 5F:
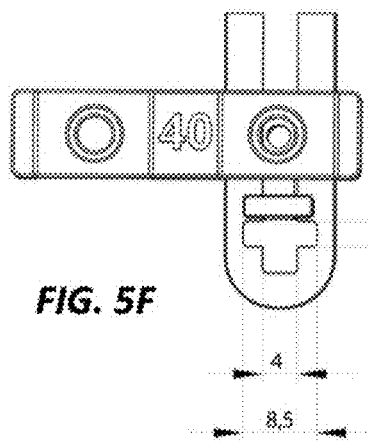
Figures 5G, 5H:
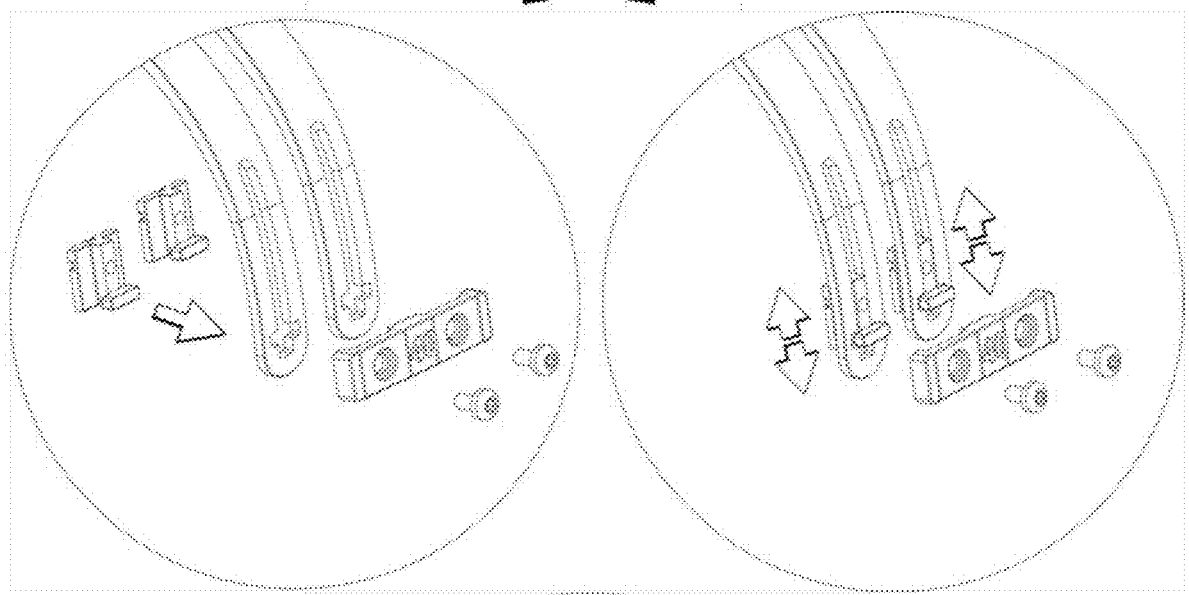
Figure 5I:
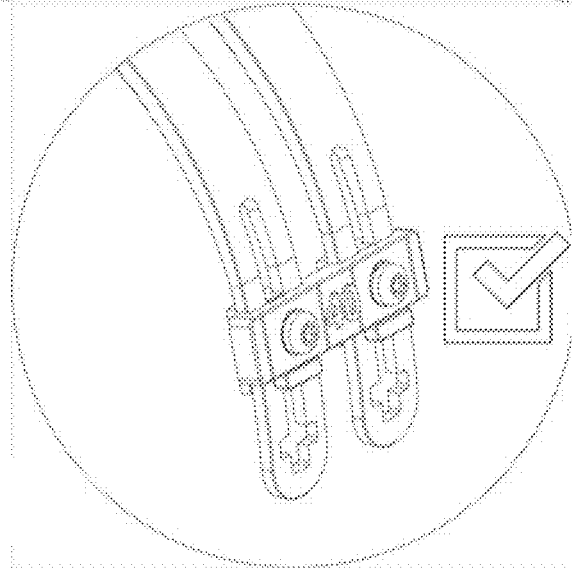
Figure 5J:
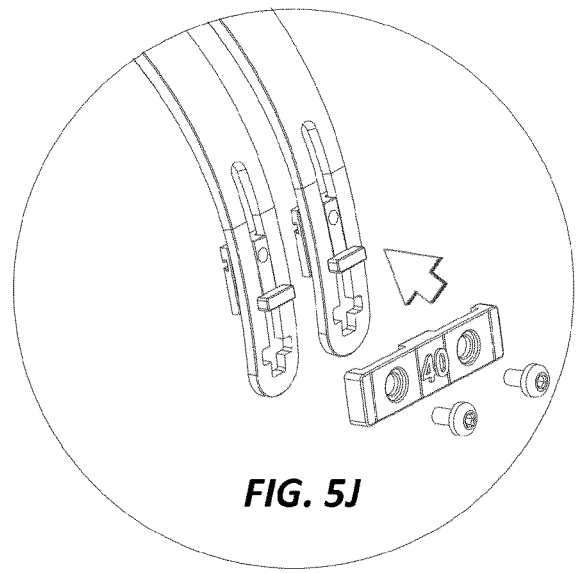
Figure 5K:
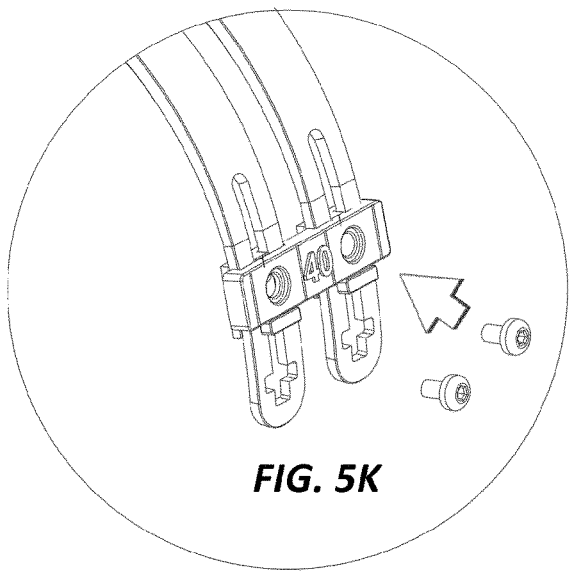
Figure 5L:
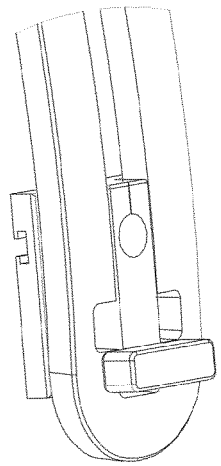
Figure 5M:
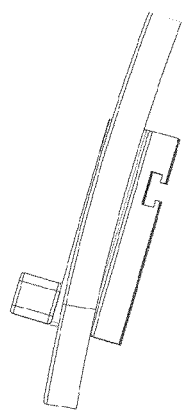
Figure 5N:
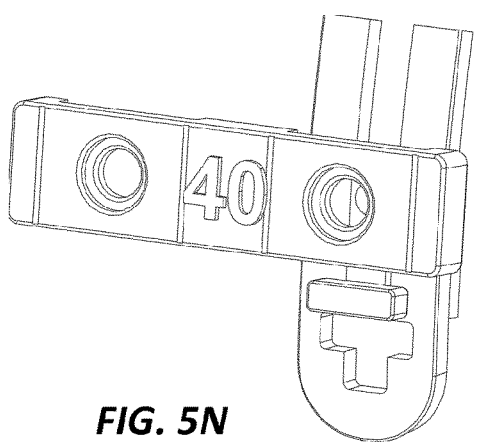
Figure 5O:
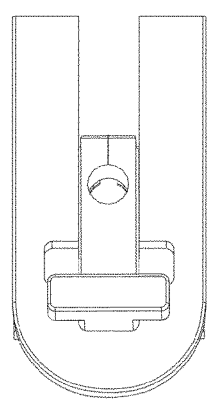

FIGS. 5A-5O show a further embodiment of the invention, where the main stabilization bar 104 includes a T-shape slot. The slider-element 106A further includes a spoiler block 500 configured to limit a range of travel for the slider-element 106A within the stabilization bar T-shape slot, where the screw and slider element assembly 106 are moveably engaged with the T-shape slot or the linear shape slot (see FIGS. 5B-5O).

Figure 6A:
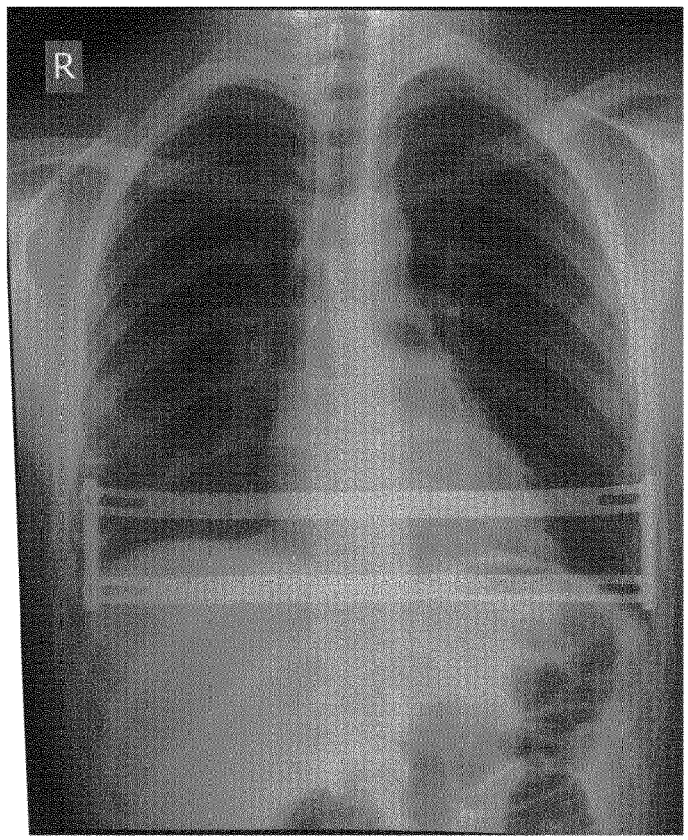
FIGS. 6A-6C show x-ray images of the different embodiments of the flail chest stabilization device implemented to patients, according to the current invention.
Figure 6B:
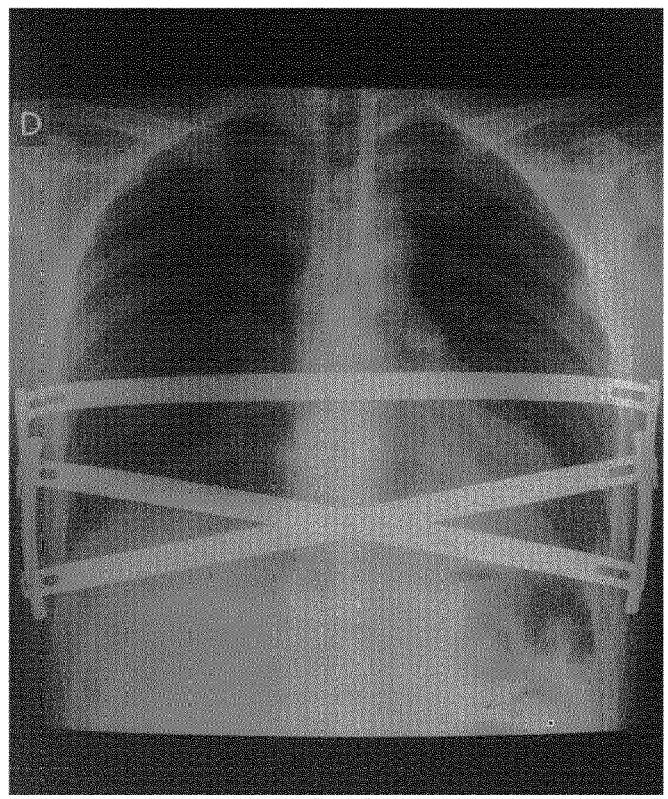
Figure 6C:
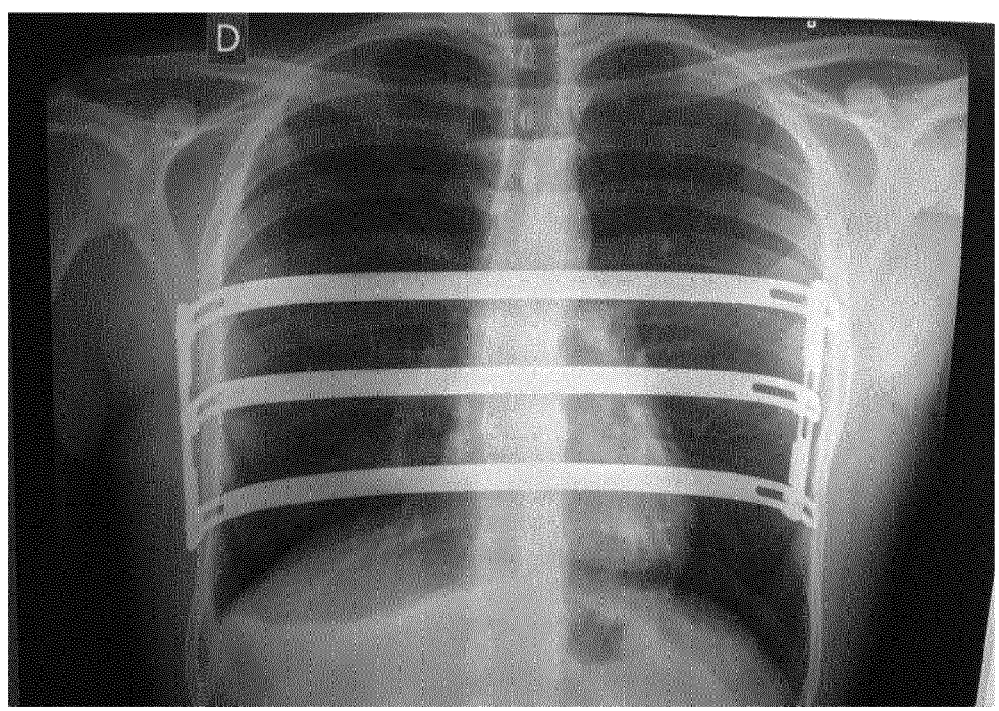

In yet another aspect of the invention, the flail chest stabilization device implants to a patient's body without connecting to a muscle, a rib or any surrounding tissue. FIGS. 6A-6C show x-ray images of the different embodiments of the flail chest stabilization device 100 implemented to patients.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, one embodiment provides a structural implant that will reshape and or stabilize the surgical remodeling of complex congenital chest wall deformities such as Currarino Syndrome, Pectus Arquatum, Poland Syndrome, Pectus Excavatum and Pectus Carinatum in all its variants and Jeune Syndrome and any variant of congenital or acquired chest wall deformity. A further embodiment provides a structural implant that will stabilize and or replace the chest wall after the surgical reconstruction and or stabilization following massive resection of chest wall sections due to chest wall tumors.

All such variations are considered to be within the scope and spirit of the present invention as defined by the following claims and their legal equivalents.

What is claimed:

1. A flail chest stabilization system, comprising:
   a) a pair of lateral bridges;
   b) a pair of main stabilization bars;
   c) a screw and slider-element connector assembly;
   d) a slider introducer tool, wherein said slider introducer tool positions said slider-element connector, wherein said main stabilization bars are connected by said screw and slider-element connector assembly to said pair of lateral bridges, wherein said stabilization bars are in a parallel configuration or crossed configuration; and
   e) a middle stabilization bar connected to said pair of lateral bridges, wherein said middle stabilization bar is configured to provide antero-posterior stabilization, wherein said middle stabilization bar is connected to said pair of lateral bridges by lateral secondary mini-bridges, wherein said lateral secondary mini-bridges are connected to said pair of lateral bridges by said screw and slider-element connector assembly, and wherein said middle stabilization bar is connected to said lateral secondary mini-bridge by a threaded screw.

2. The flail chest stabilization system of claim 1, wherein said pair of main stabilization bars have a thickness which is thicker in a center region relative to an end region of each of the pair of main stabilization bars, wherein the thickness decreases in a continuous fashion region toward each of the end regions, and wherein said thicker center region imparts a central stabilization force that is greater than an end stabilization force.

3. The flail chest stabilization system of claim 1, wherein said pair of main stabilization bars comprise a T-shape slot or a linear shape slot at each end regions, wherein said screw and slider-element connector assembly is moveably engaged with said T-shape slot or said linear shape slot.

4. The flail chest stabilization system of claim 3, wherein said screw and slider-element connector assembly further comprises a spoiler block configured to limit a range of travel for said screw and slider-element connector assembly within said T-shape slot or said linear shape slot.

5. The flail chest stabilization system of claim 1, wherein said middle stabilization bar comprises a single thickness from end to end, wherein said middle stabilization bar comprises a plurality of multiple threaded holes, or a T-shape slot or a linear shape slot on each said end.

6. The flail chest stabilization system of claim 1, wherein said middle stabilization bar is configured to impart a force that goes from front to back of a rib cage, wherein said imparted force flattens asymmetric deformities or stabilizes fractured bones.

7. The flail chest stabilization system of claim 1, wherein said flail chest stabilization device is capable of being implanted to a patient's body without attaching to a rib.

8. The flail chest stabilization system of claim 1, wherein said lateral bridges comprise a flat or curved profile.

9. The flail chest stabilization system of claim 8 further comprising a superior parallel stabilization bar, wherein said pair of main stabilization bars are connected to said pair of lateral bridges with a curved profile in said crossed configuration, or wherein said superior parallel stabilizer bar is connected to said pair of lateral bridges with a flat profile, and wherein said pair of lateral bridges with a flat profile are further connected to said main stabilization bars.

10. The flail chest stabilization system of claim 1, wherein said slider introducer tool is positioned under said main stabilization bar during a surgical procedure.

11. A flail chest stabilization device, comprising:
a) a pair of lateral bridges;
b) a pair of main stabilization bars, each having a thickness and two end regions, wherein said pair of main stabilization bars are thicker in a center region relative to each end region, wherein the thickness decreases in a continuous fashion towards each end region, and wherein said thicker center region imparts a central stabilization force that is greater than an end stabilization force; and
c) a screw and slider-element connector assembly; and
d) a middle stabilization bar connected to said pair of lateral bridges, wherein said middle stabilization bar is configured to provide antero-posterior stabilization, wherein said middle stabilization bar is connected to said pair of lateral bridges by lateral secondary mini-bridges, wherein said lateral secondary mini-bridges are connected to said pair of lateral bridges by said screw and slider-element connector assembly, and wherein said middle stabilization bar is connected to said lateral secondary mini-bridges by a threaded screw.

* * * * *